United States Patent
Mahboudi et al.

(10) Patent No.: US 11,219,843 B2
(45) Date of Patent: Jan. 11, 2022

(54) EXTRACTION OF ANIMAL-DERIVED PULMONARY SURFACTANTS

(71) Applicants: Fereidoun Mahboudi, Karaj (IR); Morteza Jaffaraghaei, Karaj (IR); Hessam Tavoli, Karaj (IR); Forugh Havasi, Karaj (IR); Maryam Maleki, Karaj (IR); Amirhosein Karagah, Karaj (IR); Abdolali Varasteh, Karaj (IR)

(72) Inventors: Fereidoun Mahboudi, Karaj (IR); Morteza Jaffaraghaei, Karaj (IR); Hessam Tavoli, Karaj (IR); Forugh Havasi, Karaj (IR); Maryam Maleki, Karaj (IR); Amirhosein Karagah, Karaj (IR); Abdolali Varasteh, Karaj (IR)

(73) Assignee: NIK PAYA KAREN PHARMED, Karaj (IR)

(*) Notice: Subject to any disclaimer, the term of this patent is extended or adjusted under 35 U.S.C. 154(b) by 5 days.

(21) Appl. No.: 16/920,510

(22) Filed: Jul. 3, 2020

(65) Prior Publication Data
US 2020/0353377 A1 Nov. 12, 2020

Related U.S. Application Data

(60) Provisional application No. 62/871,203, filed on Jul. 8, 2019.

(51) Int. Cl.
*B01D 11/02* (2006.01)
*C07K 1/14* (2006.01)
(Continued)

(52) U.S. Cl.
CPC .......... *B01D 11/0284* (2013.01); *A61K 35/42* (2013.01); *A61K 38/1709* (2013.01);
(Continued)

(58) Field of Classification Search
CPC .............. B01D 11/0284; B01D 61/147; B01D 11/0288; B01D 2239/1216; B01D 9/0054;
(Continued)

(56) References Cited

U.S. PATENT DOCUMENTS 4,312,860 A * 1/1982 Clements ............. A61K 31/685
514/78
4,338,301 A * 7/1982 Tetsuro ................... A61P 11/00
424/557
(Continued)

OTHER PUBLICATIONS

Sean B. Ainsworth et al, "Surfactant Therapy for Respiratory Distress Syndrome in Premature Neonates", 2002, Published in American Journal of Respiratory Medicine, pp. 417-433. (Year: 2002).*

*Primary Examiner* — Joseph W Drodge
(74) *Attorney, Agent, or Firm* — Bajwa IP Law Firm; Haris Zaheer Bajwa

(57) ABSTRACT

A method for extracting animal-derived pulmonary surfactants, including forming an extract of an animal lung, forming a precipitate by mixing the extract of the animal lung with a cationic flocculant solution containing poly (diallyldimethyl ammonium chloride) (pDADMAC), separating an organic phase containing pulmonary surfactants from the precipitate, recovering the pulmonary surfactants from the organic phase.

20 Claims, 7 Drawing Sheets

(51) Int. Cl.
*B01D 61/14* (2006.01)
*B01D 1/00* (2006.01)
*B01D 21/01* (2006.01)
*B01D 21/26* (2006.01)
*C07K 1/36* (2006.01)
*A61K 35/42* (2015.01)
*A61K 38/17* (2006.01)
*B01D 37/00* (2006.01)

(52) U.S. Cl.
CPC ............ *B01D 1/00* (2013.01); *B01D 11/0288* (2013.01); *B01D 21/01* (2013.01); *B01D 21/262* (2013.01); *B01D 37/00* (2013.01); *B01D 61/147* (2013.01); *C07K 1/145* (2013.01); *C07K 1/36* (2013.01); *B01D 2239/1216* (2013.01)

(58) Field of Classification Search
CPC .......... B01D 1/00; B01D 1/0011; B01D 3/00; B01D 11/02; B01D 11/028; B01D 11/04; B01D 11/0488; B01D 11/0492; B01D 17/005; B01D 17/02; B01D 17/0208; B01D 17/0217; B01D 21/01; B01D 21/26; B01D 21/262; B01D 37/00; B01D 37/03; B01D 61/14; B01D 61/145; B01D 61/20; B01D 2221/10; B01D 2311/04; B01D 2311/26; B01D 2311/2646; B01D 2311/2669; B01D 2311/2673; C07K 1/145; C07K 1/14; C07K 1/30; C07K 1/34; C07K 1/36; A01N 1/021; A01N 1/0215; A01N 1/0231; A61K 35/12; A61K 35/42; A61K 38/17; A61K 38/1709
USPC ........................................................ 424/557
See application file for complete search history.

(56) References Cited

U.S. PATENT DOCUMENTS

| | | | | |
|---|---|---|---|---|
| 4,397,839 | A * | 8/1983 | Tanaka | A61K 35/42 424/557 |
| 5,024,995 | A * | 6/1991 | Robertson | A61P 11/00 514/21.92 |
| 6,172,203 | B1 * | 1/2001 | Hager | A61K 35/42 530/412 |
| 2003/0040468 | A1 * | 2/2003 | Barron | A61P 11/00 514/1.5 |
| 2006/0205663 | A1 * | 9/2006 | Johnson | A61K 9/19 424/499 |
| 2008/0305180 | A1 * | 12/2008 | Herting | A61K 38/395 424/557 |
| 2015/0004646 | A1 * | 1/2015 | McNerney | C12P 21/02 435/69.1 |
| 2016/0264646 | A1 * | 9/2016 | Venter | C12P 21/02 |

* cited by examiner

EXTRACTION OF ANIMAL-DERIVED PULMONARY SURFACTANTS

CROSS-REFERENCE TO RELATED APPLICATION

This application claims the benefit of priority from U.S. Provisional Patent Application Ser. No. 62/871,203, filed on Jul. 8, 2019, and entitled "ANIMAL-DERIVED PULMONARY SURFACTANTS," which is incorporated herein by reference in its entirety.

TECHNICAL FIELD

The present disclosure generally relates to animal-derived pulmonary surfactants, particularly to a method for extracting animal-derived pulmonary surfactants, and more particularly to a method for extracting animal-derived pulmonary surfactants using a flocculant.

BACKGROUND

Pulmonary surfactant is a complex mixture of phospholipids and proteins that are synthesized and secreted by type II alveolar epithelial cells on a surface of a pulmonary alveolus. Components of the pulmonary surfactant coat the thin layer of the alveolus and reduce the surface tension of water; therefore, presence of the pulmonary surfactant prevents atelectasis or collapse of alveoli and allows for exchange of respiratory gases. In mammals, pulmonary surfactant contains about 10 to 12 percent protein, about 70 to 80 percent phospholipid, and about 8 percent neutralized lipid and cholesterol. Phospholipids are the main factor in reducing the surface tension with the most important phospholipid being dipalmitoylphosphatidylcholine (DPPC).

Several reasons, such as premature birth, pulmonary infection in a fetal period, bacterial infections, meconium swallowing syndrome in babies, gas poisoning, and trauma in adults may cause inadequate synthesis and secretion of the pulmonary surfactant which may contribute to severe respiratory problems such as lung atelectasis and respiratory distress syndrome. Therefore, pulmonary surfactant may be used for controlling and treating respiratory distress syndrome (RDS). Pulmonary surfactant is available in both natural and synthetic forms whereas various studies have shown that natural pulmonary surfactant leads to better results than synthetic pulmonary surfactant in therapeutic cases.

However, natural pulmonary surfactants are generally derived from mammalian lung extract requiring costly and time-consuming purification processes. Conventional purification processes are generally accompanied by using high amounts of organic and inorganic solvents, sequential high-speed centrifugations, and several filtration steps. Also, chromatography may be used during the extraction and purification steps. Therefore, there is a need for a cost-effective method for extracting pulmonary surfactants from animals with simple and fast purification processes without using chromatography techniques.

SUMMARY

This summary is intended to provide an overview of the subject matter of the present disclosure and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for extracting animal-derived pulmonary surfactants, including forming an extract of an animal lung, forming a precipitate by mixing the extract of the animal lung with a cationic flocculant solution containing poly (diallyldimethyl ammonium chloride) (pDADMAC), separating an organic phase containing pulmonary surfactants from the precipitate, and recovering the pulmonary surfactants from the organic phase. In an exemplary embodiment, separating the organic may include forming a multiphasic mixture containing the organic phase by resuspending the precipitate in an organic solvent and isolating the organic phase from the multiphasic mixture.

In an exemplary embodiment, recovering the pulmonary surfactants from the organic phase may include forming a concentrated organic phase by heating the organic phase and purifying the pulmonary surfactants from the concentrated organic phase. In an exemplary embodiment, mixing the extract of the animal lung with the cationic flocculant solution may include adding the cationic flocculant solution with a concentration of about 10% (w/v) to the extract of the animal lung with a ratio of weight of the pDADMAC to volume of the extract of the animal lung between about 0.1 g/L and about 1 g/L. In an exemplary embodiment, mixing the extract of the animal lung with the cationic flocculant solution may include mixing the extract of the animal lung with the cationic flocculant solution at room temperature for a time period between about 60 minutes and about 360 minutes. In an exemplary embodiment, the cationic flocculant solution may further include chitosan.

In an exemplary embodiment, forming the precipitate may further include incubating the precipitate for at least 1 hour at a temperature between about 2° C. and about 8° C. and centrifuging the precipitate at a speed between about 2000 relative centrifugal force (RCF) and about 3000 RCF for a time period between about 5 minutes and about 30 minutes at room temperature. In an exemplary embodiment, resuspending the precipitate in the organic solvent may include mixing the organic solvent with the precipitate with a volume ratio of the organic solvent to the precipitate between about 2 and about 4.

In an exemplary embodiment, mixing the organic solvent with the precipitate may include mixing the organic solvent with the precipitate at a speed between about 200 rpm and about 300 rpm for a time period between about 40 minutes and about 80 minutes. In an exemplary embodiment, resuspending the precipitate in the organic solvent may include adding a solution of chloroform and methanol to the precipitate. In an exemplary embodiment, isolating the organic phase from the multiphasic mixture may include incubating the multiphasic mixture at a temperature between about 2° C. and about 8° C. for a time period between about 4 hours and about 12 hours and separating the organic phase from the multiphasic mixture using a separatory funnel.

In an exemplary embodiment, forming the concentrated organic phase may include forming the concentrated organic phase with a definite volume between about 20 and about 90 times lower than a volume of the organic phase. In an exemplary embodiment, heating the organic phase may include heating the organic phase at a temperature between about 35° C. and about 55° C. under nitrogen atmosphere. In an exemplary embodiment, purifying the pulmonary surfactants from the concentrated organic phase may include forming a final mixture by mixing the concentrated organic phase with cold acetone and precipitating the pulmonary surfactants by centrifuging the final mixture.

In an exemplary embodiment, mixing the concentrated organic phase with the cold acetone may include mixing the concentrated organic phase with the cold acetone with a volume ratio of the concentrated organic phase to the cold acetone between about 1:10 and about 1:30. In an exemplary embodiment, mixing the concentrated organic phase with the cold acetone may include mixing the concentrated organic phase with the cold acetone for a time period between about 10 minutes and about 30 minutes. In an exemplary embodiment, precipitating the pulmonary surfactants may further include incubating the final mixture at a temperature of about −20° C. for a time period between about 40 minutes and about 90 minutes before centrifuging the final mixture. In an exemplary embodiment, centrifuging the final mixture may include centrifuging the final mixture at a speed between about 2000 RCF and about 3000 RCF for a time period between about 20 minutes and about 30 minutes.

In an exemplary embodiment, precipitating the pulmonary surfactants may further include drying the pulmonary surfactants under a nitrogen stream. In an exemplary embodiment, forming the extract of the animal lung may include forming a mixture by grinding the animal lung, forming a suspension by adding an electrolyte solution to the mixture, and filtering the suspension. In an exemplary embodiment, adding the electrolyte solution with the mixture may include adding the electrolyte solution to the mixture with a ratio between about 1 L/kg and about 3 L/kg of volume of electrolyte solution to weight of the mixture.

In an exemplary embodiment, adding the electrolyte solution to the mixture may include adding the electrolyte solution with a pH level between about 5.5 and about 7 at a temperature between about 20° C. and about 35° C. to the mixture. In an exemplary embodiment, forming the extract of the animal lung may include forming a suspension by lavaging the animal lung with an electrolyte solution and filtering the suspension.

Other exemplary systems, methods, features, and advantages of the implementations will be or will become, apparent to one of ordinary skill in the art upon examination of the following figures and detailed description. It is intended that all such additional systems, methods, features, and advantages be included within this description and this summary, be within the scope of the implementations and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

The present disclosure describes an exemplary fast, easy, and inexpensive method for extraction and purification of animal-derived pulmonary surfactants. In an exemplary embodiment, a flocculant may be used for separating natural surfactants of a mammalian lung. In an exemplary embodiment, the flocculant may be used in a simple and economical process instead of utilizing expensive and time-consuming methods based on multiple chromatographies, sequential high-speed centrifugations, and multiple filtrations. An exemplary method consistent with exemplary embodiments of the present disclosure may provide for an efficient and economical large-scale method for the production of pulmonary surfactants in the biotechnology and pharmaceutical industry.

Figure 1A:
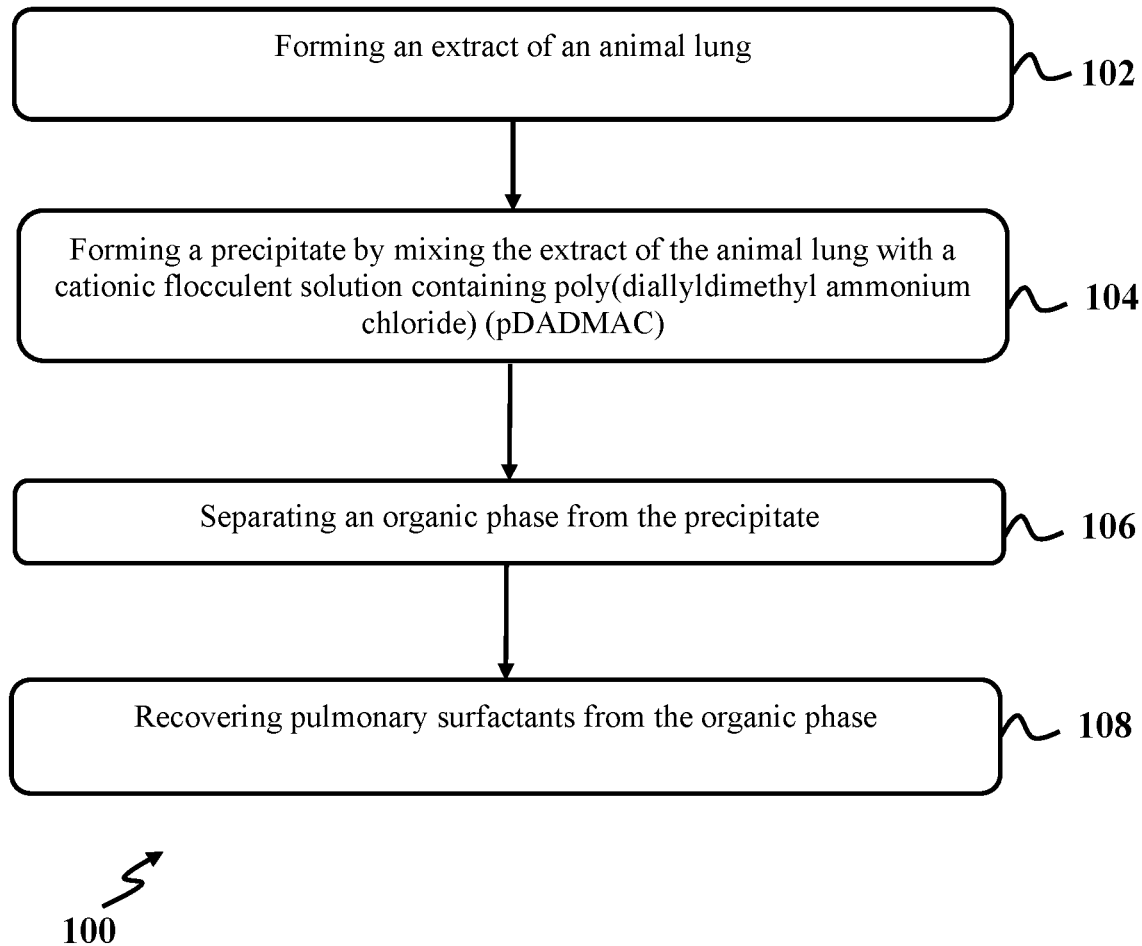
FIG. 1A shows a flowchart of an exemplary method for extracting animal-derived pulmonary surfactants, consistent with one or more exemplary embodiments of the present disclosure.

FIG. 1A shows a flowchart of an exemplary method 100 for extracting animal-derived pulmonary surfactants, consistent with one or more exemplary embodiments of the present disclosure. An exemplary method 100 may include forming an extract of an animal lung (step 102), forming a precipitate by mixing the extract of the animal lung with a cationic flocculant solution containing poly(diallyldimethyl ammonium chloride) (pDADMAC) (step 104), separating an organic phase from the precipitate (step 106), recovering pulmonary surfactants from the organic phase (step 108).

In further detail with respect to step 102, in an exemplary embodiment, forming an extract of the animal lung may include forming the extract of the animal lung by grinding the animal lung or by lavaging the animal lung. In an exemplary embodiment, the animal lung may include a lung of a mammal, such as a cow, a sheep, a goat, a camel, a horse, a pig, or a dog. In an exemplary embodiment, forming the extract of the animal lung may include forming the extract of animal lung up to 6 hours after slaughtering.

Figure 1B:
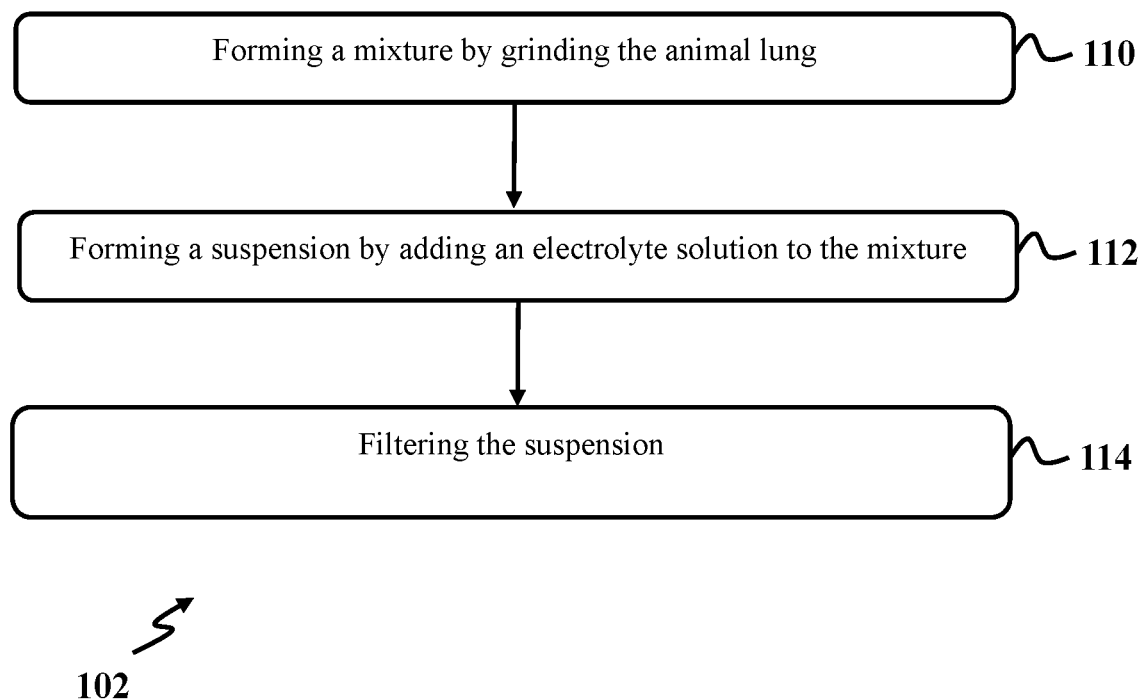
FIG. 1B shows a flowchart of an exemplary method for forming an extract of an animal lung by grinding the animal lung, consistent with one or more exemplary embodiments of the present disclosure.

FIG. 1B shows a flowchart of an exemplary method for forming an extract of an animal lung by grinding the animal lung, consistent with one or more exemplary embodiments of the present disclosure. Referring to FIG. 1B, the exemplary process may be similar to step 102 of method 100, where the exemplary process may comprise of forming the extract of the animal lung by forming a mixture by grinding the animal lung (step 110), forming a suspension by adding an electrolyte solution to the mixture (step 112), and filtering the suspension (step 114). In further detail with respect to step 110, in an exemplary embodiment, grinding the animal lung may include cutting the lung into a plurality of lung pieces and mincing the plurality of lung pieces. In an exemplary embodiment, cutting the lung into the plurality of pieces may include cutting the lung into the plurality of pieces with each piece of the plurality of pieces with a size between about 20 cm$^3$ and about 200 cm$^3$.

In further detail with respect to step 112, in an exemplary embodiment, forming the suspension may include adding an electrolyte solution to the mixture with a ratio between about 1 L/kg and about 3 L/kg of volume of electrolyte solution to weight of the mixture. In an exemplary embodiment, adding the electrolyte solution to the mixture may include mixing the electrolyte solution, with a pH level between about 5.5 and about 7 at a temperature between about 20° C. and about 35° C., with the mixture. In an exemplary embodiment, the electrolyte solution may have an ionic strength between about 10 mM and about 1000 mM. In further detail with respect to step 114, in an exemplary embodiment, filtering the suspension may include filtering the suspension utilizing a fabric filter or a bag filter at a pressure less than about 0.5 bar.

Figure 1C:
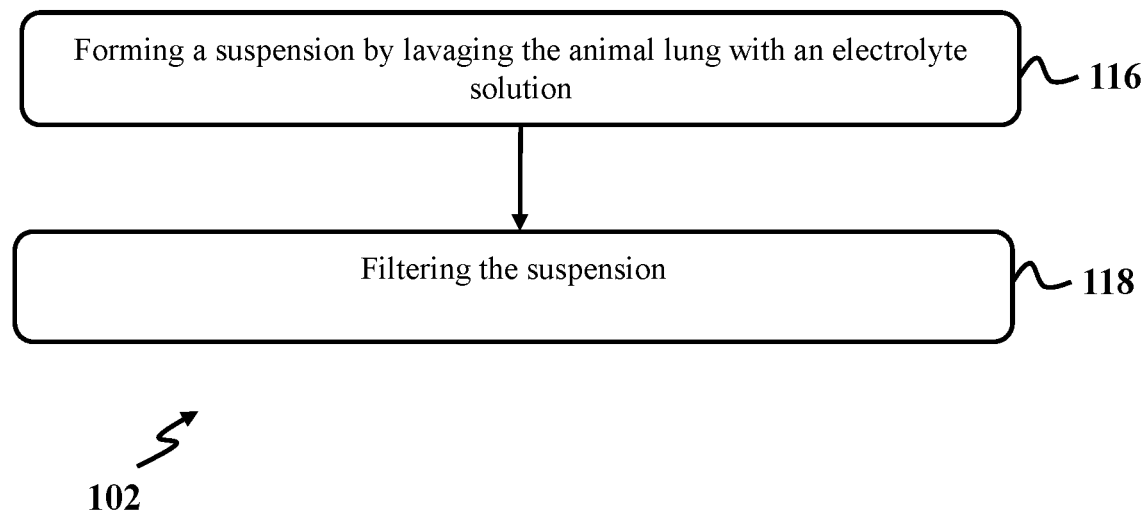
FIG. 1C shows a flowchart of an exemplary method for forming an extract of an animal lung by lavaging the animal lung, consistent with one or more exemplary embodiments of the present disclosure.

FIG. 1C shows a flowchart of an exemplary method for forming the extract of the animal lung by lavaging the animal lung, consistent with one or more exemplary embodiments of the present disclosure. Referring to FIG. 1C, the exemplary process may be similar to step 102 of method 100, where the exemplary process may comprise of forming the extract of the animal lung by forming a suspension by lavaging the animal lung with an electrolyte solution (step 116) and filtering the suspension (step 118). In further detail with respect to step 116, in an exemplary embodiment, lavaging the animal lung with the electrolyte solution may include washing out the animal lung with the electrolyte solution with an amount between about 100 ml and about 5000 ml per one lung. In an exemplary embodiment, the electrolyte solution may include physiological saline. In further detail with respect to step 118, in an exemplary embodiment, filtering the suspension may include filtering the suspension utilizing a fabric filter or a bag filter at a pressure less than about 0.5 bar.

Referring back to FIG. 1A, in further detail with respect to step 104, in an exemplary embodiment, forming a precipitate may include mixing the extract of the animal lung with a cationic flocculant solution. The term "flocculant," as used herein, refers to a substance, such as a polymer described herein, which may promote the clumping of pulmonary surfactants. In an exemplary embodiment, the cationic flocculant solution may include cationic flocculants, such as poly(diallyldimethyl ammonium chloride) (pDADMAC) which is a high charge density cationic polymer and the high charge density makes the pDADMAC well-suited for flocculation. In an exemplary embodiment, the cationic flocculant solution may further include chitosan. In an exemplary embodiment, the cationic flocculant solution may further include chitosan with a concentration between about 5 g/L and about 10 g/L. In an exemplary embodiment, the pDADMAC and the chitosan may have an anion-exchange activity with a rapid flocculating effect which leads to separation and precipitation of the pulmonary surfactants including phospholipids and lipoproteins based on their electrical charge.

In an exemplary embodiment, mixing the extract of the animal lung with the cationic flocculant solution may include adding the cationic flocculant solution to the extract of the animal lung with a ratio of weight of the pDADMAC to volume of the extract of the animal lung between about 0.1 g/L and about 1 g/L. In an exemplary embodiment, the cationic flocculant solution may be formed by dissolving the pDADMAC in a hydrophilic solvent, such as water and a normal saline solution. In an exemplary embodiment, the cationic flocculant solution may have a concentration of about 100 mg/L (10% w/v).

In an exemplary embodiment, mixing the extract of the animal lung with the cationic flocculant solution may include mixing the extract of the animal lung with the cationic flocculant solution containing the pDADMAC and the chitosan with a ratio of weight of the chitosan to volume of the extract of the animal lung between about 0.1 g/L and about 1 g/L. In an exemplary embodiment, mixing the extract of the animal lung with the cationic flocculant solution may include mixing the extract of the animal lung with the cationic flocculant solution at room temperature for a time period between about 60 minutes and about 360 minutes.

In an exemplary embodiment, forming the precipitate may further include incubating the precipitate for at least about 1 hour at a temperature between about 2° C. and about 8° C., forming a supernatant by centrifuging the precipitate at a low speed between about 2000 relative centrifugal force (RCF) and about 3000 RCF for a time period between about 5 minutes and about 30 minutes at room temperature, and removing the supernatant from the precipitate.

Figure 1D:
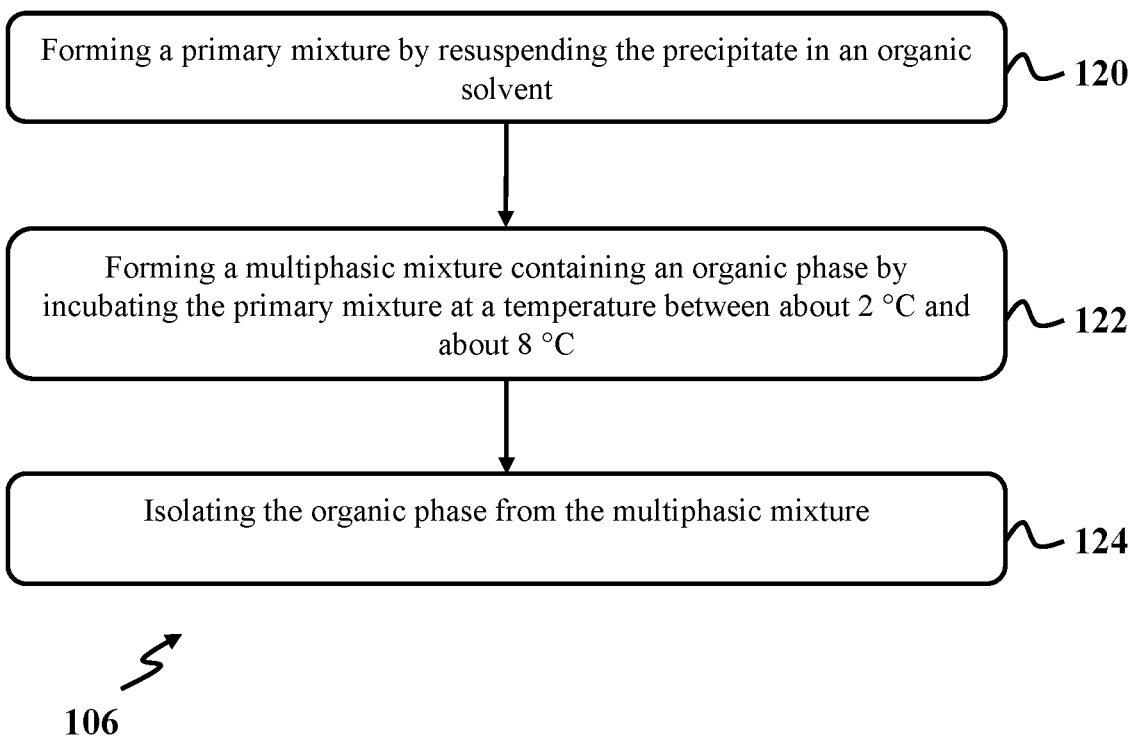
FIG. 1D shows a flowchart of an exemplary method for separating an organic phase from a precipitate, consistent with one or more exemplary embodiments of the present disclosure.

In further detail with respect to step 106, in an exemplary embodiment, separating an organic phase from the precipitate may include separating the organic phase containing the pulmonary surfactants by dissolving the precipitate in an organic solvent. FIG. 1D shows a flowchart of an exemplary method for separating the organic phase from the precipitate, consistent with one or more exemplary embodiments of the present disclosure, which may be similar to step 106. Referring to FIG. 1D, separating the organic phase from the precipitate may include forming a primary mixture by resuspending the precipitate in an organic solvent (step 120), forming a multiphasic mixture by incubating the primary mixture at a temperature between about 2° C. and about 8° C. (step 122), and isolating the organic phase from the multiphasic mixture (step 124).

In further detail with respect to step 120, in an exemplary embodiment, forming the primary mixture may include resuspending the precipitate in an organic solvent. In an exemplary embodiment, resuspending the precipitate in the organic solvent may include mixing the organic solvent with the precipitate with a volume ratio of the organic solvent to the precipitate between about 2 and about 4. In an exemplary embodiment, the organic solvent may include a solution of chloroform and methanol with a volume ratio of the chloroform to the methanol between about 1 and about 3. In an exemplary embodiment, mixing the organic solvent with the precipitate may include mixing the organic solvent with the precipitate at a speed between about 200 rounds per minute (rpm) and about 300 rpm for a time period between about 40 minutes and about 80 minutes. In an exemplary embodiment, forming the primary mixture may further include adding normal saline to the precipitate with a ratio of the normal saline to the precipitate between about 50 ml/L and about 300 ml/L prior to resuspending the precipitate in the organic solvent.

In further detail with respect to step 122, in an exemplary embodiment, forming the multiphasic mixture containing the organic phase may include incubating the primary mixture at a temperature between about 2° C. and about 8° C. for a time period between about 4 hours and about 12 hours. In an exemplary embodiment, the multiphasic mixture may comprise one of an aqueous phase, an intermediate phase, and the organic phase. In an exemplary embodiment, the organic phase as a lower phase may include the pulmonary surfactants and chloroform. In an exemplary embodiment, the aqueous phase as an upper phase may include the cationic flocculant, normal saline, and methanol. In an exemplary embodiment, the intermediate phase may include solid suspend particles.

In further detail with respect to step 124, in an exemplary embodiment, isolating the organic phase from the multiphasic mixture may include isolating the pulmonary surfactants and the chloroform from other phases of the multiphasic mixture using a separatory funnel or decanter.

Figure 1E:
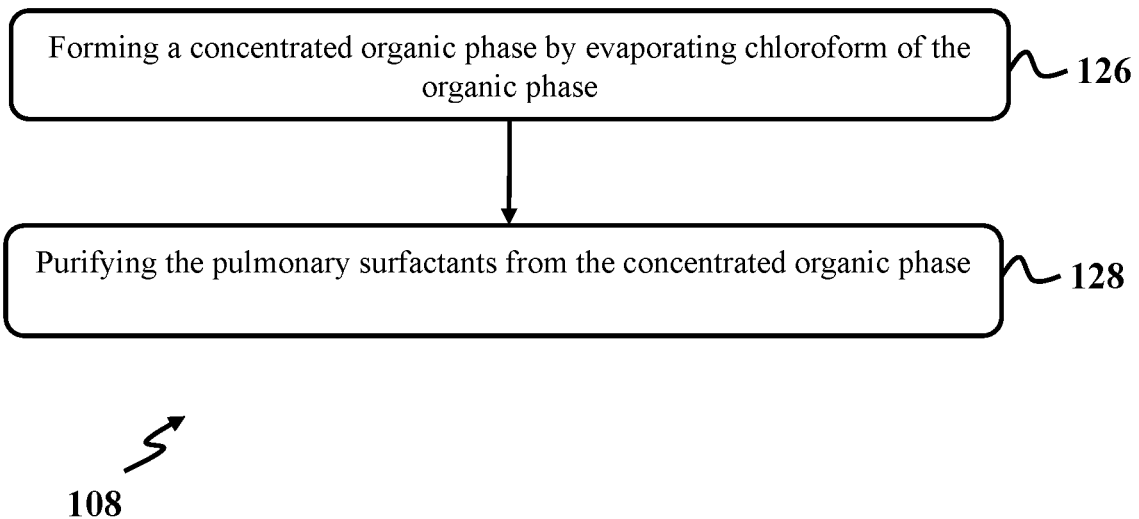
FIG. 1E shows a flowchart of an exemplary method for recovering pulmonary surfactants from an organic phase, consistent with one or more exemplary embodiments of the present disclosure.

Referring back to FIG. 1A, in further detail with respect to step 108, in an exemplary embodiment, the exemplary method may include recovering pulmonary surfactants from the organic phase. FIG. 1E shows a flowchart of an exemplary method for recovering the pulmonary surfactants from the organic phase, consistent with one or more exemplary embodiments of the present disclosure, similar to step 108. Referring to FIG. 1E, recovering the pulmonary surfactants from the organic phase may include forming a concentrated organic phase by evaporating chloroform of the organic phase (step 126) and purifying the pulmonary surfactants from the concentrated organic phase (step 128).

In further detail with respect to step 126, forming the concentrated organic phase may include concentrating the organic phase. In an exemplary embodiment, concentrating the organic phase may include evaporating chloroform of the organic phase using at least one technique of rotary evaporation, vacuum distillation, and atmospheric distillation. In an exemplary embodiment, concentrating the organic phase may include evaporating the chloroform at a temperature between about 35° C. and about 55° C. under a nitrogen stream. In an exemplary embodiment, the nitrogen stream may have a maximum flow rate of about 2 L/min. In an exemplary embodiment, forming the concentrated organic phase may include forming the concentrated organic phase with a definite volume between about 20 and about 90 times lower than a volume of the organic phase.

In further detail with respect to step 128, purifying the pulmonary surfactants from the concentrated organic phase may include forming a final mixture by mixing the concentrated organic phase with cold acetone and precipitating the lung surfactants by centrifuging the final mixture. In an exemplary embodiment, the cold acetone may have a temperature between −10° C. and −40° C. In an exemplary embodiment, mixing the concentrated organic phase with the cold acetone may reduce cholesterol impurity of the pulmonary surfactants to a concentration less than about 1.2% w/w through the dissolution of cholesterol in the cold acetone.

In an exemplary embodiment, mixing the concentrated organic phase with the cold acetone may include mixing the concentrated organic phase with the cold acetone with a volume ratio of the concentrated organic phase to the cold acetone between about 1:10 and about 1:30. In an exemplary embodiment, mixing the concentrated organic phase with the cold acetone may include mixing the concentrated organic phase with the cold acetone at a speed between about 50 rpm and about 500 rpm for a time period between about 10 minutes and about 30 minutes. In an exemplary embodiment, centrifuging the final mixture may include centrifuging the final mixture at a speed between about 2000 RCF and about 3000 RCF for a time period between about 20 minutes and about 30 minutes.

In an exemplary embodiment, purifying the pulmonary surfactants may further include drying the pulmonary surfactants under a nitrogen stream. In an exemplary embodiment, the pulmonary surfactants may include dipalmitoylphosphatidylcholine (DPPC) with a ratio of the DPPC/total phospholipid between about 30% and about 50%. In an exemplary embodiment, the pulmonary surfactants may include protein with a concentration between about 0.5% and about 10% of the total weight of the pulmonary surfactants.

In an exemplary embodiment, formulated pulmonary surfactants may be formed by dissolving the pulmonary surfactants in a formulation buffer including sodium chloride (NaCl). In an exemplary embodiment, the formulation buffer may include NaCl with a concentration of about 154 mM at a pH level between about 6.1 and about 6.3 at a temperature between about 35° C. and about 40° C. In an exemplary embodiment, the formulated pulmonary surfactant may be clarified through filtration with a pore size between about 4 μm and about 8 μm and then may be filled in sterile vials. In an exemplary embodiment, sterile vials may be autoclaved and sterilized for a time period of about 3 minutes at a temperature of about 135° C. or for a time period of about 20 minutes at a temperature of about 121° C.

In an exemplary embodiment, the formulated pulmonary surfactant may be used for controlling and treating respiratory distress syndrome (RDS). In an exemplary embodiment, the formulated pulmonary surfactant with an effective amount between about 2 mg/kg birth weight and about 5 mg/kg birth weight may be administered to a patient. In an exemplary embodiment, the formulated pulmonary surfactant may be administered directly into an airway of a mammal in need thereof. In an exemplary embodiment, the formulated pulmonary surfactant may be administered via an endotracheal tube.

EXAMPLES

Example 1: Extraction of Animal-Derived Pulmonary Surfactants

In this example, animal-derived pulmonary surfactants were extracted and purified through a process similar to method 100 as described in FIG. 1A. At first, respiratory tubes, vessels, blood clots, and unwanted tissues of fresh lungs of healthy mammals, such as sheep, cow, and goat were removed up to 6 hours after slaughtering and the lungs were fragmented to about first size slices. After that, a lung mixture was formed by adding an electrolyte solution such as physiologic saline with a pH level between about 5.5 and 7 and at a temperature of about 30° C. to 35° C. to fragmented lung pieces at a concentration of about 3 liters per kilogram tissue. The lung mixture was then blended using a blender and filtered using a fabric filter or a bag filter to form an extract of the animal lung.

In the next step, in order to perform precipitation and primary separation of the pulmonary surfactants, a cationic flocculant solution containing polydiallydimethylammonium chloride (pDADMAC) was used. The extract of the animal lung is a complex mixture of different types of macromolecules, cells, and cell-derived components from minced lung tissue, in which, the cationic flocculant solution of the pDADMAC was used to flocculate and precipitate the pulmonary surfactants with a negative charge from other impurities.

Therefore, a precipitate was formed by adding a pDADMAC solution to the lung mixture under continuous stirring with a ratio of weight of the pDADMAC to volume of the lung mixture of about 0.2 g/L under continuous stirring. The pDADMAC solution had a concentration of about 100 mg/L (10% w/v). Then, the precipitate was completely formed by incubating at a temperature between about 2° C. and about 8° C. for at least 2 hours. Also, the supernatant may be gently removed and the precipitate was separated by a technique such as low-speed centrifugation method at a temperature of about 4° C. The low-speed centrifugation method was used at a speed between about 2000 RCF and about 3000 relative centrifugal force (RCF).

In the next step, an organic phase containing the pulmonary surfactants was separated from the precipitate by mixing an organic solvent with the precipitate. The organic solvent containing chloroform and methanol with a volume ratio of (chloroform:methanol) 2:1 was added to the precipitate. In an exemplary embodiment, the volume of the organic solvent was about three times the volume of the precipitate. The resulting mixture was stirred for a time period between about 40 minutes to about 80 minutes at a speed between 200 rpm and 300 rpm and then incubated for a time period between 4 hours and 12 hours at a temperature between about 2° C. and about 8° C.

Compounds of the pulmonary surfactants are soluble in organic solvents, such as chloroform, but pDADMAC is soluble in aqueous solvents and not soluble in the organic solvent. Therefore, the solubility difference of the cationic flocculant solution (pDADMAC) and the pulmonary surfactants in the organic solvent was used for phase partitioning during incubation. After incubation, a multiphasic mixture containing three phases was created. The three phases included a lower phase containing surfactant components (liposoluble components) in chloroform, a middle phase containing solid suspended particles, and a top aqueous phase containing the cationic flocculant solution (pDADMAC) and methanol. Then, the organic phase containing chloroform and surfactant phase was separated from other phases using a separation funnel or a decanter.

In the next step, pulmonary surfactants were recovered from the organic phase by forming a concentrated organic phase and purifying the pulmonary surfactants. The concentrated organic phase was formed by evaporating the chloroform of the organic phase in a stream of nitrogen to reach a volume of about one-eightieth (1/80) of the volume of the organic phase. The maximum flow rate of the nitrogen stream was about 2 L/min at a temperature between 35° C. and 45° C. In order to enhance the purity and reduce the amount of the natural lipids, such as cholesterol, in the final product to a concentration of less than 1.2%, the concentrated organic phase was slowly added to cold acetone at a temperature of about −20° C. under continuous stirring. The volume ratio of acetone to the pulmonary surfactant mixture was 20 to 1.

The resulting mixture was stirred for a time period between 10 minutes to 30 minutes; and then it was incubated at a temperature of about −20° C. for a time period between 40 minutes and 80 minutes. During incubation, cholesterol was dissolved in acetone and pulmonary surfactant compounds like phospholipids and lipoproteins were precipitated. After that, the precipitated pulmonary surfactant was separated by low-speed centrifugation and was dried using a stream of nitrogen. After drying, the precipitated pulmonary surfactant was preserved in chloroform at a temperature between about 2° C. to 8° C.

In order to produce the final formulation, the pulmonary surfactants were precipitated out again from the chloroform solution using cold acetone (−20° C.). Then, the pulmonary surfactants were mixed and dissolved in a formulation buffer containing NaCl with a concentration of about 154 mM at a temperature between 35° C. and 40° C. After that, the formulated pulmonary surfactants were clarified through filtration using filters with a pore size between about 4 μm and about 8 μm and then filled in sterile vials. The vials were autoclaved and sterilized for 3 minutes at a temperature of about 135° C.

Example 2: Physicochemical Characterization of the Exemplary Pulmonary Surfactants In this example, the physicochemical characterization of the exemplary pulmonary surfactants including surface properties and component compositions were assessed. TABLE. 1 represents the surface properties including surface tension of four batches of the exemplary pulmonary surfactants and a commercial pulmonary surfactant at temperatures of 25° C. and 37° C. The commercial pulmonary surfactant used in this example was a commercial extract of natural porcine lung surfactant. Referring to TABLE. 1, surface tension reduction ability of all batches of the exemplary pulmonary surfactant of the present disclosure were similar to the commercial pulmonary surfactant at temperatures of 25° C. and 37° C. Therefore, regarding the surface properties, the exemplary pulmonary surfactant and the commercial pulmonary surfactant did not have any significant difference with each other.

TABLE 1

Surface properties of the exemplary pulmonary surfactants

| Pulmonary surfactant samples | Surface tension at 25° C. (mN/m) | Surface tension at 37° C. (mN/m) |
| --- | --- | --- |
| Commercial pulmonary surfactant | 22.28 | 14.79 |
| Exemplary pulmonary surfactant (Batch 1) | 18.18 | 14.42 |
| Exemplary pulmonary surfactant (Batch 2) | 18.77 | 14.3 |
| Exemplary pulmonary surfactant (Batch 3) | 22.31 | 19.95 |
| Exemplary pulmonary surfactant (Batch 4) | 21.24 | 16.9 |

Figure 2A:
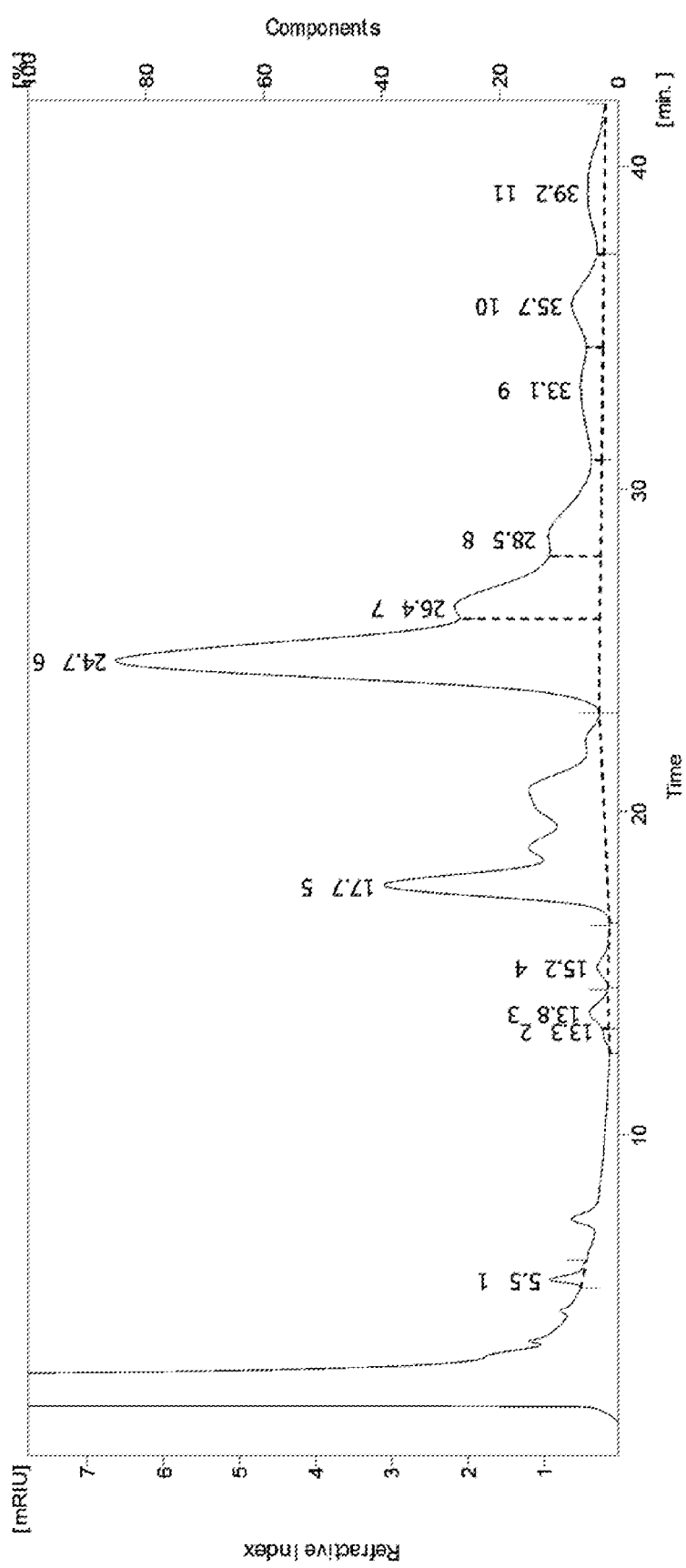
FIG. 2A shows a reversed-phase high-performance liquid chromatography (RP-HPLC) chromatogram of exemplary animal-derived pulmonary surfactants extracted using an exemplary method, consistent with one or more exemplary embodiments of the present disclosure.

FIG. 2A shows a reversed-phase high-performance liquid chromatography (RP-HPLC) chromatogram of the exemplary pulmonary surfactants, consistent with one or more exemplary embodiments of the present disclosure. TABLE. 2 also represents extracted data of the RP-HPLC chromatogram of the exemplary pulmonary surfactants of the present disclosure.

TABLE 2

Extracted data from the RP-HPLC chromatogram of the exemplary pulmonary surfactants

| No. | Retention Time [min] | Area [μRIU · s] | Area [%] | Compound Name |
|---|---|---|---|---|
| 1 | 5.500 | 70.345 | 0.6 | Palmitic Acid |
| 2 | 13.250 | 20.926 | 0.2 | Cholesterol |
| 3 | 13.767 | 99.060 | 0.8 | Phospholipid |
| 4 | 15.183 | 60.982 | 0.5 | Phospholipid |
| 5 | 17.733 | 3102.108 | 24.9 | Phospholipid |
| 6 | 24.683 | 5383.483 | 43.2 | Phospholipid (DPPC) |
| 7 | 26.350 | 1590.391 | 12.8 | Phospholipid |
| 8 | 28.467 | 793.598 | 6.4 | Phospholipid |
| 9 | 33.100 | 487.861 | 3.9 | Phospholipid |
| 10 | 35.700 | 485.683 | 3.9 | Phospholipid |
| 11 | 39.200 | 373.778 | 3.0 | Phospholipid |
| Total | | 12468.217 | 100.0 | |
| Total phospholipid | | 2376.946 | | |
| DPPC/Total phospholipid | | 0.432 | | |

Figure 2B:
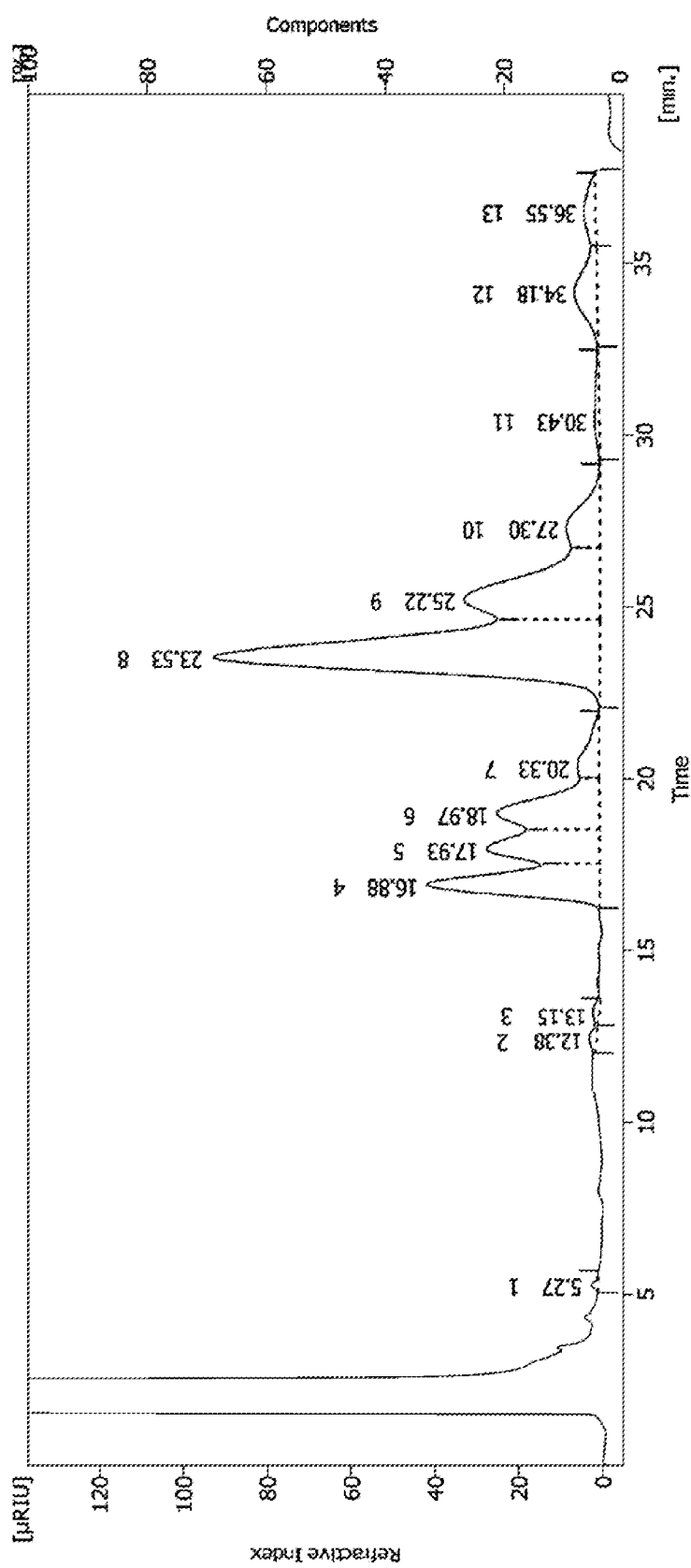
FIG. 2B shows an RP-HPLC chromatogram of commercial animal-derived pulmonary surfactants, consistent with one or more exemplary embodiments of the present disclosure.

FIG. 2B shows an RP-HPLC chromatogram of a commercial pulmonary surfactant, consistent with one or more exemplary embodiments of the present disclosure. TABLE. 3 represents extracted data from the RP-HPLC chromatogram of the commercial pulmonary surfactant.

TABLE 3

Extracted data from the RP-HPLC chromatogram of the commercial pulmonary surfactants

| No. | Retention Time [min] | Area [μRIU · s] | Area [%] | Compound Name |
|---|---|---|---|---|
| 1 | 5.26 | 22.12 | 0.1 | Palmitic Acid |
| 2 | 12.38 | 35.62 | 0.2 | Cholesterol |
| 3 | 13.15 | 28.86 | 11 | Phospholipid |
| 4 | 16.88 | 1760.66 | 8.6 | Phospholipid |
| 5 | 17.93 | 1308.96 | 9.5 | Phospholipid |
| 6 | 18.96 | 1454.99 | 2.2 | Phospholipid |
| 7 | 20.33 | 330.29 | 40. | Phospholipid |
| 8 | 23.53 | 6211.95 | 17. | Phospholipid (DPPC) |
| 9 | 25.21 | 2666.16 | 4.1 | Phospholipid |
| 10 | 27.30 | 621.50 | 0.6 | Phospholipid |
| 11 | 30.43 | 90.53 | 3.2 | Phospholipid |
| 12 | 34.18 | 484.64 | 1.5 | Phospholipid |
| 13 | 36.55 | 221.38 | 100.0 | Phospholipid |
| Total | | 15237.719 | | |
| Total phospholipid | | 15179.97 | | |
| DPPC/Total phospholipid | | 0.41 | | |

Generally, in order to adjust to adjust the concentration of dipalmitoylphosphatidylcholine (DPPC) as the most important component of the pulmonary surfactants in natural surfactant products, the DPPC is typically added to the conventional natural surfactant products. However, a comparison between the data of TABLE 2 and TABLE 3 indicates that the ratio of DPPC/total phospholipid in the exemplary pulmonary surfactants is higher than the commercial pulmonary surfactant. Therefore, there is not any need for the addition of the DPPC to the exemplary pulmonary surfactants of the present disclosure. Referring to FIGS. 2A-2B and TABLEs 2-3, the exemplary pulmonary surfactants of the present disclosure were similar to the commercial pulmonary surfactant in terms of component compositions including phospholipids, lipoproteins, neutralizing lipids, and cholesterol.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, the inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A method for extracting animal-derived pulmonary surfactants, comprising:
    forming an extract of an animal lung;
    forming a precipitate by mixing the extract of the animal lung with a cationic flocculant solution, the cationic flocculant solution comprising poly(diallyldimethyl ammonium chloride) (pDADMAC);
    separating an organic phase containing pulmonary surfactants from the precipitate, comprising:
        forming a multiphasic mixture containing the organic phase by resuspending the precipitate in an organic solvent; and
        isolating the organic phase from the multiphasic mixture; and
    recovering the pulmonary surfactants from the organic phase, comprising:
        forming a concentrated organic phase by heating the organic phase; and
        purifying the pulmonary surfactants from the concentrated organic phase.

2. The method of claim 1, wherein mixing the extract of the animal lung with the cationic flocculant solution comprises adding the cationic flocculant solution with a concentration of 10% (w/v) to the extract of the animal lung with a ratio of weight of the pDADMAC to volume of the extract of the animal lung between 0.1 g/L and 1 g/L.

3. The method of claim 2, wherein mixing the extract of the animal lung with the cationic flocculant solution comprises mixing the extract of the animal lung with the cationic flocculant solution at room temperature for a time period between 60 minutes and 360 minutes.

4. The method of claim 1, wherein mixing the extract of the animal lung with the cationic flocculant solution comprises mixing the extract of the animal lung with the cationic flocculant solution containing the pDADMAC and chitosan.

5. The method of claim 4, wherein mixing the extract of the animal lung with the cationic flocculant solution comprises mixing the extract of the animal lung with the cationic flocculant solution containing the pDADMAC and the chitosan with a ratio of weight of the chitosan to volume of the extract of the animal lung between 0.1 g/L and 1 g/L.

6. The method of claim 1, wherein forming the precipitate further comprises:
    incubating the precipitate for at least 1 hour at a temperature between 2° C. and 8° C.; and
    centrifuging the precipitate at a speed between 2000 relative centrifugal force (RCF) and 3000 RCF for a time period between 5 minutes and 30 minutes at room temperature.

7. The method of claim 1, wherein resuspending the precipitate in the organic solvent comprises mixing the organic solvent with the precipitate with a volume ratio of the organic solvent to the precipitate between 2 and 4.

8. The method of claim 7, wherein mixing the organic solvent with the precipitate comprises mixing the organic solvent with the precipitate at a speed between 200 rpm and 300 rpm for a time period between 40 minutes and 80 minutes.

9. The method of claim 1, wherein resuspending the precipitate in the organic solvent comprises adding a solution of chloroform and methanol with a volume ratio of the chloroform to the methanol between 1 and 3 to the precipitate.

10. The method of claim 1, wherein isolating the organic phase from the multiphasic mixture comprises:
    incubating the multiphasic mixture at a temperature between 2° C. and 8° C. for a time period between 4 hours and 12 hours; and
    separating the organic phase from the multiphasic mixture using a separatory funnel.

11. The method of claim 1, wherein forming the concentrated organic phase comprises forming the concentrated organic phase with a definite volume between 20 and 90 times lower than a volume of the organic phase.

12. The method of claim 1, wherein heating the organic phase comprises heating the organic phase at a temperature between 35° C. and 55° C. under nitrogen atmosphere.

13. The method of claim 1, wherein purifying the pulmonary surfactants from the concentrated organic phase comprises:
    forming a final mixture by mixing the concentrated organic phase with cold acetone at a temperature between −10° C. and −40° C.; and
    precipitating the pulmonary surfactants by centrifuging the final mixture.

14. The method of claim 1, wherein mixing the concentrated organic phase with the cold acetone comprises mixing the concentrated organic phase with the cold acetone with a volume ratio between 1:10 and 1:30 of the concentrated organic phase to the cold acetone.

15. The method of claim 13, wherein mixing the concentrated organic phase with the cold acetone comprises mixing the concentrated organic phase with the cold acetone at a speed between 50 rpm and 500 rpm for a time period between 10 minutes and 30 minutes.

16. The method of claim 1, wherein precipitating the pulmonary surfactants may further include incubating the final mixture at a temperature of −20° C. for a time period between 40 minutes and 90 minutes before centrifuging the final mixture.

17. The method of claim 1, wherein centrifuging the final mixture comprises centrifuging the final mixture at a speed between 2000 relative centrifugal force (RCF) and 3000 RCF for a time period between 20 minutes and 30 minutes.

18. The method of claim 1, wherein forming the extract of the animal lung comprises:

forming a mixture by grinding the animal lung;
forming a suspension by adding an electrolyte solution to the mixture; and
filtering the suspension.

19. The method of claim 18, wherein adding the electrolyte solution with the mixture comprises adding the electrolyte solution to the mixture with a ratio between 1 L/kg and 3 L/kg of volume of electrolyte solution to weight of the mixture.

20. The method of claim 18, wherein adding the electrolyte solution to the mixture comprises adding the electrolyte solution with a pH level between 5.5 and 7 at a temperature between 20° C. and 35° C. to the mixture.

\* \* \* \* \*